United States Patent [19]

Laico et al.

[11] Patent Number: 4,930,523
[45] Date of Patent: Jun. 5, 1990

[54] SURGICAL SHOULDER POSITIONING APPARATUS

[75] Inventors: Joseph P. Laico, New City; Joseph L. Molino, Valley Cottage, both of N.Y.

[73] Assignee: Lincoln Mills, Inc., New City, N.Y.

[21] Appl. No.: 337,333

[22] Filed: Apr. 13, 1989

[51] Int. Cl.$^5$ .............................................. A61F 13/00
[52] U.S. Cl. ..................................... 128/845; 128/84 R
[58] Field of Search ................. 128/84 R, 84 A, 84 B, 128/69, 71, 75; 248/278, 279; 269/328; 5/63, 81, 89

[56] References Cited

U.S. PATENT DOCUMENTS

| | | | |
|---|---|---|---|
| 2,550,983 | 5/1951 | Ettinger | 128/84 C |
| 2,631,582 | 3/1953 | Bensfield | 128/84 C |
| 3,659,594 | 5/1972 | Schwab | 128/69 |
| 3,693,617 | 9/1972 | Trott | 128/84 B |
| 4,445,506 | 5/1984 | Johansson et al. | 128/84 C |
| 4,534,341 | 8/1985 | Bart et al. | 128/69 |
| 4,616,637 | 10/1986 | Caspari et al. | 128/84 R |
| 4,621,625 | 11/1986 | Powlan | 128/84 C |
| 4,644,595 | 2/1986 | Daniel | 128/69 |
| 4,674,484 | 6/1987 | Kott | 128/69 |
| 4,679,552 | 7/1987 | Caspari | 128/84 R |

Primary Examiner—Robert A. Hafer
Assistant Examiner—Charles H. Sam
Attorney, Agent, or Firm—Chilton, Alix & Van Kirk

[57] ABSTRACT

A surgical shoulder positioning apparatus comprises a pivotally positionable abductor boom. An abductor collar and an arm extender may be suspended from the boom. The boom is variably positionable to obtain the proper abduction orientation of a shoulder for shoulder surgery. The abductor boom is mounted on a crossbar extending between a pair of upright support frames which are mounted to the operating table.

17 Claims, 2 Drawing Sheets

SURGICAL SHOULDER POSITIONING APPARATUS

BACKGROUND OF THE INVENTION

This invention relates generally to devices which are employed for positioning the limbs of a patient for medical procedures. More particularly, this invention relates devices which are employed for positioning the shoulder and arm of a patient.

A number of devices have been advanced to provide for the proper positioning of limbs for therapeutic or medical purposes. In this regard, complex traction systems employing cords and pulleys have conventionally been employed to obtain and maintain the proper positioning. In surgical procedures to which the invention relates, a positioning apparatus is required to "open" the joint to allow for insertion of surgical instruments while immobilizing the associated joint and limb at a fixed position for a given time and readily permitting repositioning to subsequent succeeding fixed positions. In arthroscopic surgical procedures performed on the shoulder of a patient, the optimum abduction position of the shoulder/arm ordinarily ranges between a 25° and 45° angle of abduction relative to a horizontal axis. The present invention has particular applicability in connection with maintaining the proper shoulder abduction angle for arthroscopic surgery procedures or for any surgical procedures performed on the shoulder and proximal regions.

SUMMARY OF THE INVENTION

Briefly stated, the invention in a preferred form is an apparatus which is adapted for positioning the shoulder of a patient for arthroscopic surgery or other surgical procedures. The apparatus includes a pair of laterally spaced support members which are mounted in parallel upright disposition. Table clamps mount the members to the rails of the operating table. A crossbar extends laterally relative to the support members. A manually operable drive mechanism is mounted to the crossbar for variably displacing a positioning shaft. A second crossbar laterally extends relative to the support members to mount a boom. The boom generally transversely extends from a forward end to a rear end. A pivotal linkage connects the rear end with the positioning shaft. An abduction sling assembly is suspended from the boom for supporting the upper arm and for abducting the upper arm to provide a separating or abducting force on the shoulder. The forearm is provided with longitudinal traction by attaching a well padded forearm holder and applying a tensional force to the forearm. Upon placing the arm of a patient in the abduction sling assembly, the forward end of the boom may be selectively raised and lowered by manual operation of the drive mechanism to abduct the shoulder of the patient.

In one apparatus embodiment, the drive assembly comprises a crank which is manually angularly displaceable for displacing the positioning shaft. The sling assembly includes a collar which is suspended from the forward end of the boom by means of a cord. A tension indicating device connects the cord at the forward end of the boom for indicating the tension exerted against the collar. The abductor sling also comprises an arm extender of padded flexible form which is attachable to the arm of the patient for extension of the arm. The extender includes a cord which is mounted to two pulleys and connected to a weight train. The support members may be generally L-shaped members. The boom may be variably laterally positionable relative to the second crossbar.

An object of the invention is to provide a new and improved shoulder positioning apparatus for obtaining and maintaining the proper angle of abduction of the shoulder and the arm.

Another object of the invention is to provide a new and improved surgical shoulder positioning apparatus having an efficient construction wherein the abduction and longitudinal traction of an arm/shoulder may be obtained and maintained in an efficient manner which does not unduly interfere with the surgical procedure.

A further object of the invention is to provide a new and improved shoulder positioning apparatus which is easily adaptable for use on an operating table to obtain the proper abduction and separation of a patient's arm/shoulder for arthroscopic surgery and other medical procedures.

Other objects and advantages of the invention will become apparent from the drawings and the specification.

DETAILED DESCRIPTION OF THE INVENTION

Figure 1:
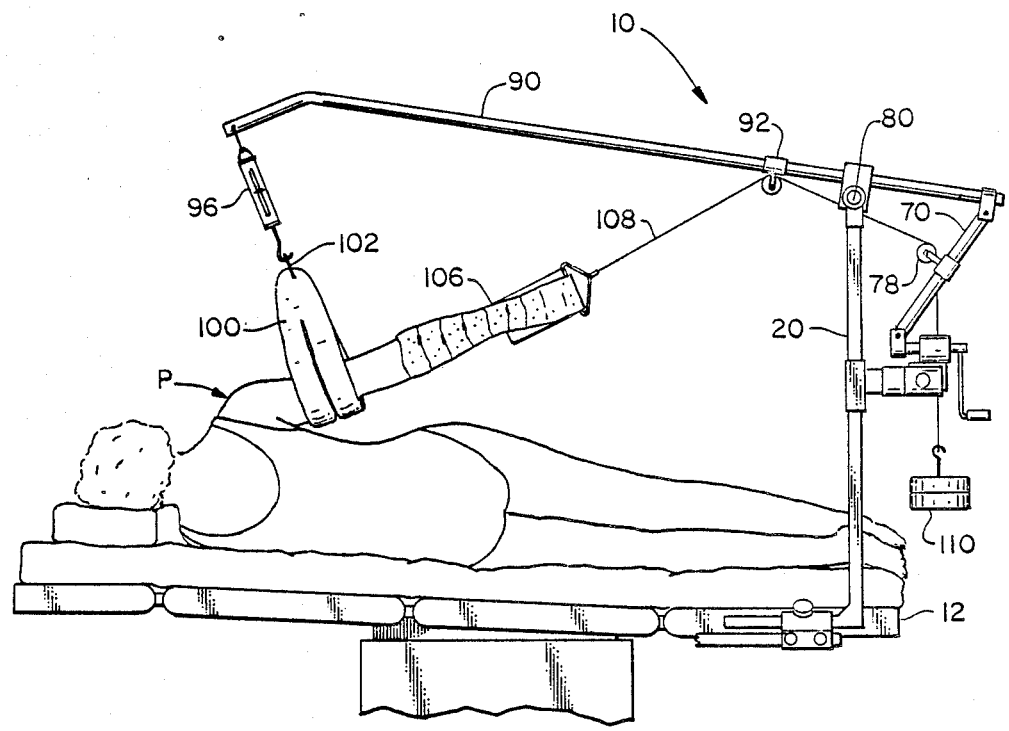
FIG. 1 is a fragmentary perspective view of a surgical shoulder positioning apparatus of the present invention illustrated in conjunction with a patient.
Figure 2:
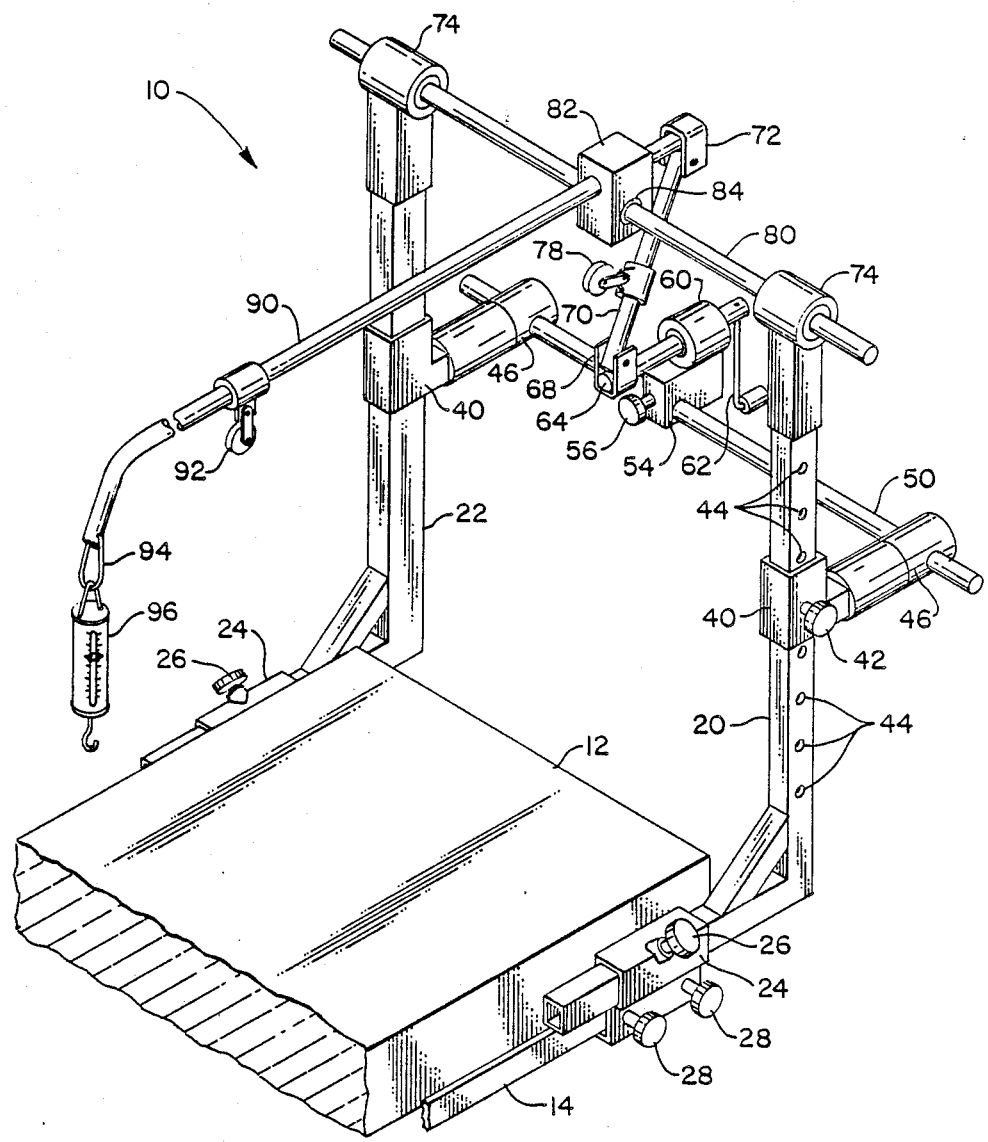
FIG. 2 is a fragmentary perspective view of the shoulder positioning apparatus of FIG. 1.

With reference to the drawings wherein like numerals represent like parts throughout the figures, a surgical shoulder positioning apparatus in accordance with the present invention is generally designated by the numeral 10. The shoulder positioning apparatus 10, in its preferred application, is adapted for mounting to an operating table 12 for maintaining the proper abduction and separation of a shoulder/arm for purposes of arthroscopic surgery or other surgical procedures. For purposes of illustration in FIG. 1, the shoulder positioning apparatus is connected to a patient P in a fixed operative position for performing surgery on the shoulder of the patient.

The optimal abduction angle ordinarily lies in the range of between 25° and 45° to the horizontal axis. The proper abduction position will vary in accordance with a given patient and the procedure to be performed and may also change during the course of the operation. While apparatus 10 has other applications, the shoulder positioning apparatus 10 is especially adapted for efficiently obtaining and maintaining the proper abduction of the shoulder for arthroscopic surgical procedures.

The apparatus 10 is adapted for mounting to an operating table 12 for disposition generally above the patient P. The apparatus connects to separate locations of the lower and upper arm of patient P so as to abduct the shoulder and thereby separate the shoulder joint, as will be detailed below. The operating table 12 includes rails 14 of conventional form and function which are preferably used to mount the shoulder positioning apparatus.

A pair of substantially identical upright support members 20 and 22 are secured to the operating table by means of table clamps 24. Support members 20 and 22 may be manufactured from rectangular or rounded tubular steel or similar materials. The support members have a generally L-shaped configuration, including a diagonal brace. The legs of the support members are received in slides of the table clamps 24 and secured in fixed position to the table clamps by means of a knob operable clamp screw 26. A second set of manually operable clamp screws 28 secure the table clamps to the operating table rails 14 at a fixed position along the rails. The upright support members 20 and 22 project above the operating table in a generally parallel vertical orientation. The apparatus is longitudinally positionable along the rails 14 of the operating table, as required. During usage, the longitudinal position is securely fixed by the clamp screws 26 and 28.

A pair of substantially identical bracket connectors 40 are slidably mounted to the support members. The connectors 40 form a slot which is dimensioned to be approximately commensurate with the section of the support members 20 and 22 so that the connectors are engageable slidable along the supports. The connectors are secured in a rigid, fixed intermediate position by means of a clamp screw 42. The screw 42 is threadable through the side of the connector and receivable in one of a vertical series of apertures 44 of the support member for securely locking each bracket connector in the fixed vertical position.

A pair of corresponding connector bosses 46 extend rearwardly from the bracket connectors 40 for receiving a crossbar 50. Crossbar 50 extends in a generally horizontal orientation through the bosses 46. A connector block 54 is slidably received on the crossbar 50. A clamp screw 56 threaded to block 54 tightens against the crossbar to secure the block 54 at a fixed lateral position along the crossbar 50.

The top of the connector block 54 has an opening (not illustrated) which receives a stud (not illustrated) projecting downwardly from a crank housing 60 for mounting the crank housing to the connector block. A crank 62 extends rearwardly from the crank housing 60. Manual rotatable movement of the crank 62 results in a longitudinal displacement of a positioning shaft 64 which essentially reciprocates relative to the housing 60. The crank housing encloses a screw and a threaded interior end portion of the positioning shaft 64. For example, a clockwise rotation to the crank threadably displaces the positioning shaft 64 from the housing. A counter-clockwise rotation threadably retracts the positioning shaft into the housing. The position of the shaft 64 determines the abduction angle.

A swivel connector 68 is rigidly connected at the end of the positioning shaft 64. A lower end of a rod-like arm 70 is pivotally connected to the swivel connector 68. The upper end of the arm 70 is pivotally connected to a second swivel connector 72. A pulley 78 is mounted to the arm 70 at a fixed intermediate location.

A pair of substantially identical yokes 74 mount over the top portion of the upright support members 20 and 22. A crossbar 80 similar to crossbar 50 extends between the yokes in a generally horizontal orientation. Crossbar 80 is also parallel to crossbar 50. A connector block 82 having two orthogonal through bores is slidably received by the crossbar 80. The connector block 82 is secured in adjustably fixed lateral position by means of elastomeric collars 84. The collars 84 are positioned against lateral sides of the connector block and resiliently, frictionally engage against the crossbar 80 to prevent movement of the connector block 82 along the crossbar. The collars 84 may be laterally displaced to change the lateral position of the connector block.

An elongated abductor boom 90 of bent or angled configuration extends through the block 82 to connect in a fixed transverse relationship to the connector block. The rear portion of the abductor boom 90 rigidly connects with the swivel connector 72. A longitudinally positionable pulley 92 is mounted to the abductor boom 90. A loop 94 at the end of the boom secures a tension scale 96. The tension scale may assume a wide variety of forms. In one embodiment, the tension scale 96 is capable of readings from 0 to 30 pounds.

With reference to FIG. 1, a cervical collar 100 is adapted to be secured to patient P under the upper arm biceps portion. The collar 100 connects via a cord 102 fastened to a hook at the end of the tension scale 96 for suspension from the front end of the abductor boom. The upward tension exerted by the collar functions to abduct the patient's shoulder. The tension scale 96 provides an indicator for monitoring the abduction tension during the medical procedure.

A padded arm holder 106 of flexible material is wrapped around the lower portion of the arm and hand. A tension cord 108 leads from the outer end portion of the arm holder 106 upward through boom pulley 92 and pulley 78 which is mounted to the fulcrum arm. The end of the cord is secured to a weight tray 110. The tension exerted through the cord to the arm holder functions to extend the arm. Pulley 92 may also be attached to crossbar 80 or 50 or arm 70.

The shoulder positioning apparatus 10 provides an efficient means for correctly positioning the shoulder of a patient for arthroscopic surgery or other surgery and other related procedures. The cervical collar 100 is positioned under the upper arm of the patient. The holder 106 is wrapped around the lower arm/hand portion. The abductor boom 90 is manually raised or lowered through crank 62 to the proper height for abducting the upper arm and shoulder. The tension of the cord 108 functions to extend the arm straight out from the shoulder.

The correct positioning and/or repositioning of the shoulder is obtained by the crank handle. Upon rotary movement of the crank handle, the positioning shaft 64 connects via the arm 70 linkage for raising and lowering, as desired, the abductor boom. The extension of the arm is maintained during the raising and lowering process. In one embodiment of the invention, the end of the boom has a vertical displacement of approximately 40 inches from the maximum to the minimum position of the crank drive fulcrum 64.

The lateral position of the abductor boom 90 relative to the patient may be suitably obtained by sliding the connector blocks 54 and 82 along the respective crossbars. The blocks 54 and 82 are secured in position by the respective set screw 56 and locating collars 84. The shoulder abduction is obtained without causing undo interference with the surgical procedure.

While a preferred embodiment of the invention has been set forth for purposes of illustration, the foregoing description should not be deemed a limitation of the invention herein. Accordingly, various modifications, adaptations, and alternatives may occur to one skilled in the art without departing from the spirit and the scope of the present invention.

What is claimed:
1. A shoulder positioning apparatus comprising:

support means for providing a pair of laterally spaced support members;

mounting means for mounting said support means to an operating table for generally parallel upright disposition of said support members;

first crossbar means mounted to said support members at an intermediate position thereof comprising a first crossbar extending laterally relative to said support members;

manually operable drive means mounted to said first crossbar for variably displacing a positioning shaft;

p1 second crossbar means mounted to said support frames comprising a second crossbar extending laterally relative to said support members;

boom means mounted to said second crossbar comprising a boom generally transversely extending relative to said support members, said boom having a forward end and a rear end and a pivotal linkage connecting said rear end and said positioning shaft;

abduction sling means suspended from said boom for supporting said upper arm, so that upon placing the arm of a patient in said abduction sling means, the forward end of said boom may be selectively raised and lowered by manual operation of aid drive means to abduct and thereby separate the shoulder of the patient.

2. The shoulder positioning apparatus of claim 1 wherein said drive means comprises a housing and a crank which is angularly displaceable for displacing said positioning shaft relative to said crank housing.

3. The shoulder positioning apparatus of claim 1 wherein said abduction sling means further comprising a collar suspended from said forward end of said boom for securement under the upper arm of a patient.

4. The shoulder positioning apparatus of claim 3 wherein said abduction sling means further comprises a cervical collar and a cord extending from said collar.

5. The shoulder positioning apparatus of claim 4 further comprising a tension indicating device connecting with said cord and the forward end of said boom for indicating the tension exerted against said collar.

6. The shoulder positioning apparatus of claim 1 further comprising a first pulley mounted to said boom and a second pulley mounted to said linkage.

7. The shoulder positioning apparatus of claim 6 wherein said abduction sling means further comprises arm extender means attachable to the arm of a patient for extension of said arm.

8. The shoulder positioning apparatus of claim 7 wherein said arm extender means further comprises a cord and a weight tray, said cord mounting to said first and second pulleys and connecting with said weight tray.

9. The shoulder positioning apparatus of claim 1 wherein said support members are generally L-shaped members.

10. The shoulder positioning apparatus of claim 1 wherein said mounting means are table clamps mountable to laterally spaced rails.

11. The shoulder positioning apparatus of claim 1 wherein said boom may be variably laterally positionable relative to said second crossbar and further comprising securement means for fixing the lateral position.

12. A shoulder positioning apparatus comprising:

frame means for providing a pair of laterally spaced support frames;

mounting means for mounting said frame members for generally parallel upright disposition of said support frames;

first crossbar means mounted to said support members at an intermediate position thereof comprising a first crossbar extending laterally relative to said support members;

crank means comprising a housing, a crank and a positioning member displaceable relative to said housing in response to rotary motion of said crank, said crank means being mounted to said first crossbar for variably displacing said positioning member relative to said crank housing;

second crossbar means mounted to said support frames comprising a second crossbar extending laterally relative to said support frames;

boom means mounted to said second crossbar comprising a boom generally transversely extending relative to said support frames, said boom having a forward end and a rear end and a pivotal linkage connecting said rear end and said positioning member;

shoulder abductor means suspended from said boom for connecting under the upper arm region of a patient for abduction thereof, arm extension means for connecting at a lower arm portion of said patient for extension thereof;

so that said shoulder abductor means and said arm extension means may be concurrently raised and lowered by manual operation of said crank means.

13. The shoulder positioning apparatus of claim 12 further comprising tension indicating means for indicating the tension exerted between said forward boom and said shoulder abductor means.

14. The shoulder positioning apparatus of claim 12 wherein said arm extension means further comprises a weight tray, a cord and pulley means said cord extending through said pulley means for exerting tension along said cord.

15. A shoulder positioning apparatus comprising:

frame means comprising a pair of laterally spaced support members mounted in generally parallel upright relationship;

first crossbar means mounted to said support members comprising a first crossbar extending laterally relative to said support members;

shaft means mounted to said first crossbar comprising a shaft and positioning means for variably positioning said shaft;

second crossbar means mounted to said support members comprising a second crossbar extending relative to said support members;

boom means mounted to said second crossbar comprising a boom generally transversely extending relative to said support members, said boom having a forward end and a rear end and a linkage pivotally connecting said rear end and said shaft;

shoulder abductor means for connecting under the upper arm region of a patient for abduction and separation thereof;

arm extension means suspended from said boom for connecting at a lower arm region of said patient for extension of said arm;

so that upon connecting said shoulder abductor means and arm extension means to a patient, said boom may be positioned by said positioning means for abducting the shoulder of the patient at a selected orientation.

16. The shoulder positioning apparatus of claim 15 further comprising tension indicating means for indicating the tension exerted between said boom and said shoulder abductor means.

17. The shoulder positioning apparatus of claim 15 wherein said arm extension means further comprises a weight tray, a cord and pulley means, said cord extending through said pulleys means for exerting tension along said cord.

* * * * *